United States Patent
Carbunaru et al.

(10) Patent No.: US 8,965,524 B2
(45) Date of Patent: Feb. 24, 2015

(54) EXTERNAL DEVICE FOR AN IMPLANTABLE MEDICAL SYSTEM HAVING ACCESSIBLE CONTRAINDICATION INFORMATION

(71) Applicant: Boston Scientific Neuromodulation Corporation, Valencia, CA (US)

(72) Inventors: Rafael Carbunaru, Valley Village, CA (US); Que Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/461,426

(22) Filed: Aug. 17, 2014

(65) Prior Publication Data

US 2014/0358190 A1    Dec. 4, 2014

Related U.S. Application Data (63) Continuation of application No. 14/061,326, filed on Oct. 23, 2013, now Pat. No. 8,812,129, which is a continuation of application No. 12/498,061, filed on Jul. 6, 2009, now Pat. No. 8,588,925.

(51) Int. Cl.
- *A61N 1/00* (2006.01)
- *A61N 1/372* (2006.01)
- *A61N 1/36* (2006.01)

(52) U.S. Cl.
CPC ........ *A61N 1/37252* (2013.01); *A61N 1/36071* (2013.01); *A61N 1/37229* (2013.01)
USPC .................... 607/60; 607/30; 607/32; 607/38

(58) Field of Classification Search
USPC .......................... 607/30, 32, 38, 60
See application file for complete search history.

(56) References Cited

U.S. PATENT DOCUMENTS

| | | | |
|---|---|---|---|
| 6,411,840 B1 | 6/2002 | Bardy | |
| 6,516,227 B1 | 2/2003 | Meadows et al. | |
| 6,694,186 B2 | 2/2004 | Bardy | |
| 6,704,595 B2 | 3/2004 | Bardy | |
| 6,826,425 B2 | 11/2004 | Bardy | |
| 6,904,312 B2 | 6/2005 | Bardy | |
| 7,177,698 B2 | 2/2007 | Klosterman et al. | |
| 7,302,291 B2 | 11/2007 | Bardy | |
| 7,697,994 B2 | 4/2010 | VanDanacker | |
| 7,787,958 B2 | 8/2010 | Stevenson | |
| 7,853,322 B2 | 12/2010 | Bourget | |
| 7,916,013 B2 | 3/2011 | Stevenson | |
| 7,945,322 B2 | 5/2011 | Stevenson | |
| 8,214,042 B2 | 7/2012 | Ozawa et al. | |
| 8,244,367 B2 | 8/2012 | Wahlstrand | |
| 8,335,569 B2 | 12/2012 | Aghassian | |

(Continued)

*Primary Examiner* — Nicole F Lavert
(74) *Attorney, Agent, or Firm* — Lewis & Reese, PLLC (57) ABSTRACT

Disclosed is a remote controller for an implantable medical device having stored contraindication information, which includes information which a patient or clinician might wish to review when assessing the compatibility of a given therapeutic or diagnostic technique or activity with the patient's implant. The stored contraindication information is available through a display of the remote controller or via a wired, wireless, or portable drive connection with an external device. By storing contraindication information with the implant's remote controller, patient and clinician can more easily determine the safety of a particular therapeutic or diagnostic technique or physical activity with the patient's implant, perhaps without the need to contact the manufacturer's service representative.

42 Claims, 7 Drawing Sheets

(56) References Cited

U.S. PATENT DOCUMENTS

| | | |
|---|---|---|
| 8,498,716 B2 | 7/2013 | Chen et al. |
| 2007/0060980 A1 | 3/2007 | Strother |
| 2008/0027500 A1 | 1/2008 | Chen |
| 2008/0051668 A1 | 2/2008 | Bardy |
| 2009/0024179 A1 | 1/2009 | Dronov |
| 2010/0305663 A1 | 12/2010 | Aghassian |
| 2010/0318159 A1 | 12/2010 | Aghassian et al. |

EXTERNAL DEVICE FOR AN IMPLANTABLE MEDICAL SYSTEM HAVING ACCESSIBLE CONTRAINDICATION INFORMATION

CROSS REFERENCE TO RELATED APPLICATIONS

This is a continuation application of U.S. patent application Ser. No. 14/061,326, filed Oct. 23, 2013 (pending), which is a continuation application of U.S. patent application Ser. No. 12/498,061, filed Jul. 6, 2009 (now U.S. Pat. No. 8,588,925), which are both incorporated by reference, and to which priority are claimed.

TECHNICAL FIELD

The present invention relates to the field of implantable medical devices, and in particular, to external devices that contain information related to the patient and the implantable medical device system.

BACKGROUND ART

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227.

Figure 1:
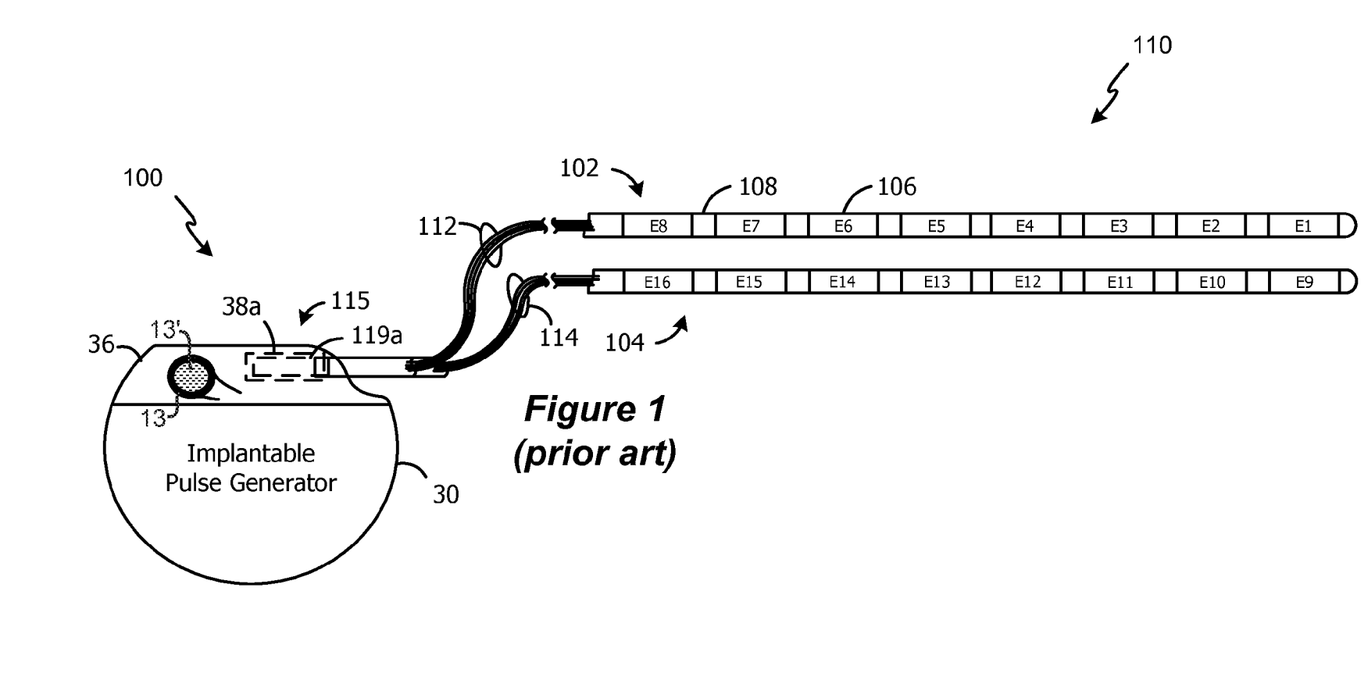
FIG. 1 is a block diagram illustrating conventional implantable medical devices according to the prior art.

Spinal cord stimulation is a well-accepted clinical method for reducing pain in certain populations of patients. As shown in FIG. 1, a SCS system typically includes an Implantable Pulse Generator (IPG) 100, which includes a biocompatible case 30 formed of titanium, for example. The case 30 typically holds the circuitry and power source or battery necessary for the IPG 100 to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled E1-E8, and eight electrodes on lead 104, labeled E9-E16, although the number of leads and electrodes is application specific and therefore can vary.

Figure 2:
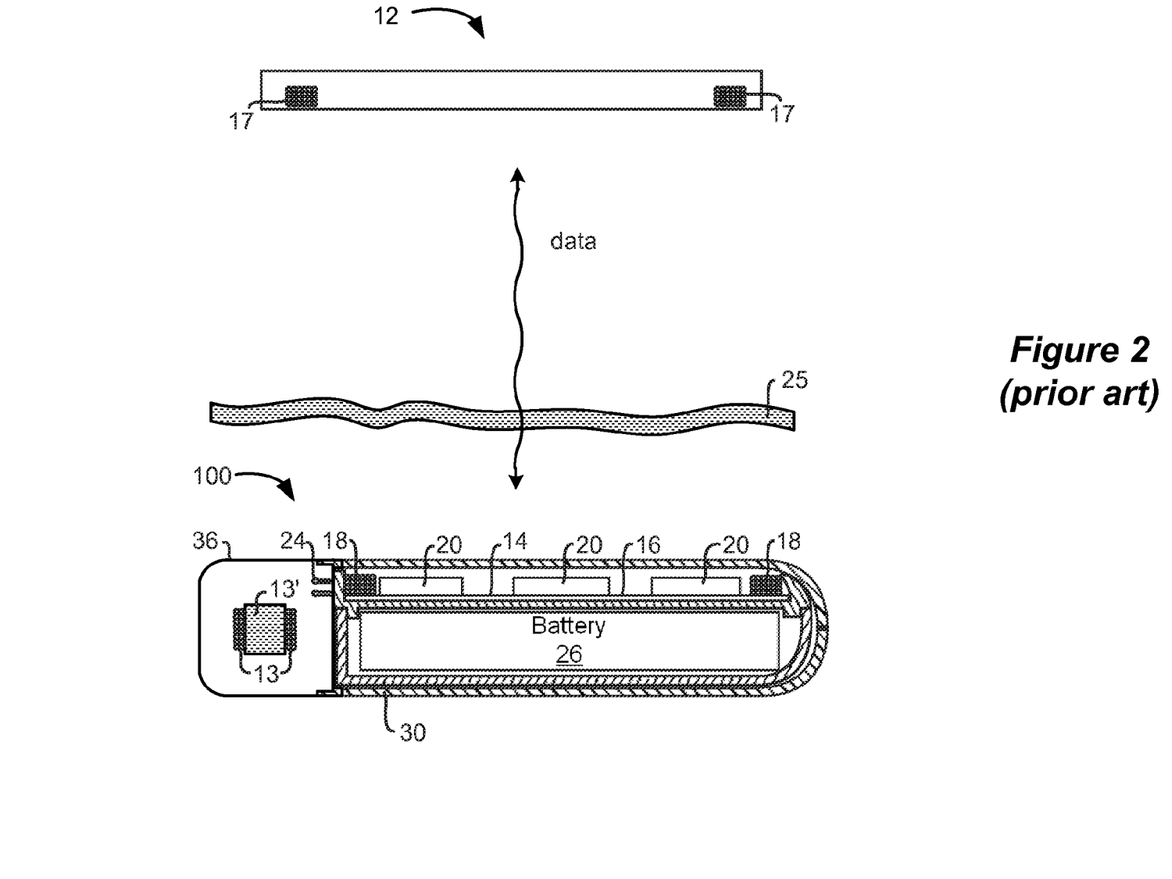
FIG. 2 is a block diagram illustrating the use of a remote controller to communicate with an implantable medical device according to the prior art.

FIG. 2 shows portions of an IPG system in cross section, including the IPG 100 and a remote controller 12. The IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from the remote controller 12, and a charging coil 18 for charging or recharging the IPG's power source or battery 26 using an external charger (not shown). The telemetry coil 13 can be mounted within the header connector 36 as shown.

A remote controller 12 is used to communicate with and control a patient's IPG 100. Such external control is beneficial, because a patient's stimulation needs may change throughout the day. For example, different therapy settings may be required for when the patient is sleeping, standing, sitting, or driving. Some settings are saved as "presets" or "programs" and can be selected by the patient using the remote controller 12. As well as being useable to select a particular therapy program, the remote controller 12 can be used to increase or decrease stimulation strength, select different areas of the body or electrodes to be stimulated, and to shut off and turn on stimulation. In addition, the remote controller 12 can act as a receiver of data from the IPG 100, receiving various data reporting on the IPG 100's status. Remote controller 12 is hand-held and portable.

The communication of data from the remote controller 12 to the IPG 100 occurs via magnetic inductive coupling. When data is to be sent from the remote controller 12 to the IPG 100, coil 17 is energized with an alternating current (AC). Such energizing of the coil 17 to transfer data can occur using a Frequency Shift Keying (FSK) protocol for example, such as disclosed in U.S. Patent Publication 2009/0024179 (pending). Energizing the coil 17 induces an electromagnetic field, which in turn induces a current in the IPG's telemetry coil 13, which current can then be demodulated to recover the original data.

As is well known, inductive transmission of data or power occurs transcutaneously, i.e., through the patient's tissue 25, making it particular useful in a medical implantable device system.

Clinicians treating patients with implantable medical devices that they have not implanted or are not familiar with may have doubts about the use of various therapeutic or diagnostic techniques on such patients. For example, the clinician or the patient may have concerns related to the compatibility of certain therapeutic or diagnostic techniques with the patient's implant, such as use of computerized tomography (CT) scans, magnetic resonance imaging (MRI), diathermy, transcutaneous electrical nerve stimulation (TENS), etc. Patients may also be worried about the compatibility with other non-medical related activities, such as running, swimming, contact sports, taking an airplane, going through X-ray checkpoints, etc., and to what extent such activities are contraindicated by the patient's implant.

Usually such concerns take time to be addressed since the patient or clinician may need to contact the manufacturer of the implant system or its service representative regarding the proposed therapeutic or diagnostic technique or desired activity and relevant contraindications arising from the implanted medical device. While patient manuals or clinician manuals provided with the implant system may contain the desired information, patients and clinicians rarely have the information available when needed.

DESCRIPTION OF EMBODIMENTS

Implant system manufacturers regularly receive phone calls regarding implant patients that need to undergo certain therapeutic or diagnostic medical procedures, or that wish to partake in some sort of activity such as contact sports. While in many cases the information desired by the patient or clinician is present in the manuals provided with the implant system, patients and clinicians may still call the manufacturer's technical support representative to inquire about the implantable medical device because the manual is not available to them at the time the information is needed. Even if the patient has the manuals, the patient or clinician may still have doubts regarding the compatibility of certain therapeutic or diagnostic procedures or of various other activities with the patient's implant, which doubts may arise because of some particular medical condition or sensitivity of the patient that is not addressed by the manuals.

To alleviate this problem, the embodiments disclosed below provide contraindication information in an improved remote controller 200 associated with the patient's implantable medical device. Such "contraindication information" includes one or more of the following pieces of information which a patient or clinician might wish to review when assessing the compatibility of a given therapeutic or diagnostic technique or other activity with the patient's implant: the patient or clinician's manuals for the implant system, including the manuals for the implant and any associated external devices (e.g., remote controllers or external chargers); any specific contraindicated therapeutic or diagnostic techniques or activities; contact information for the manufacturer of the implant system or its service representative; clinician contact information, for example the contact information of the clinician who implanted the implant, or another clinician having information relevant to the use of particular therapeutic or diagnostic techniques or other contraindicated or compatible activities; clinician instructions regarding therapeutic or diagnostic techniques or activities compatible with or contraindicated by the patient's implant; patient history or patient records relevant to a particular therapeutic or diagnostic techniques or activities compatible with or contraindicated by the patient's implant; etc. As referred to herein, "contraindication indication" also indicates procedures or activities that are compatible with the patient's implant as well as those that are prohibited, at least to some conditional degree.

Such contraindication information can be stored with the remote controller 200 at the time of the implant system's manufacture (e.g., manufacture contact information; manuals), while other information can be stored later (e.g., clinician contact information; patient history). The contraindication information can be conveyed to the patient or clinician directly via the remote controller's user interface, e.g., the display associated with the remote controller. Alternatively, the stored contraindication information may be conveyed to the clinician or patient via a connection with a computer, a personal digital assistant (PDA), or similar device. The connection may be wired, e.g., a Universal Serial Bus (USB), serial port, or parallel port connection; wireless, e.g., BLUETOOTH®, WI-FI®, or infrared connections; or can comprise a portable removable storage device such as a memory card or a USB thumb drive. Hardware and communication links for storing and retrieving contraindication information in and from the remote controller are discussed in further detail herein.

Clinicians or patients able to access the contraindication information stored with the remote controller 200 can take proactive measures against contraindicated procedures and activities, therefore improving patient safety. Clinician, patient, and the implant system manufacturer can also download additional contraindication information to the remote controller later to improve even further the accuracy and usefulness of the information going forward. Because the remote controller is used often by the patient and is easily accessible to the patient or clinician, providing contraindication information with the remote controller eases confusion and uncertainty when the patient requires a particular contraindicated procedure. Convenient access to contraindication information is further facilitated due to the hand-held or portable nature of the remote controller.

The description that follows relates to use of the invention within a spinal cord stimulation (SCS) system. However, the present invention is not so limited. Rather, the present invention can be used with any type of implantable medical device system that could benefit from an enhanced remote controller. For example, the present invention can be used as part of a system employing an implantable sensor, an implantable pump, a pacemaker, a defibrillator, a cochlear stimulator, a retinal stimulator, or in any other neural stimulator configured to treat any of a variety of conditions.

Disclosed are various embodiments by which relevant contraindication information can be associated with the patient's remote controller 200. As shown in one example in FIG. 3A, the improved remote controller 200 provides contraindication information on a removable storage 300. To accommodate removable storage 300, the remote controller 200 includes a removable storage interface 319 into which the removable storage 300 can be inserted or to which the removable storage 300 can otherwise be coupled. Removable storage 300 are typically small thin cards containing memory intended for removable data storage, and typically comprise flash EEPROM memory. At present, common forms of removable storage 300 comprise Secure Digital (SD®), Mini SD, MICRO SD®, SD HC®, or MEMORY STICK® memory cards, etc. Some removable storage interfaces 319 can be used with a variety of different removable storage 300. Removable storage 300 are available in a variety of memory capacities from numerous sources. A typical removable storage 300 may have at least 1 GB of storage capacity, although smaller or larger capacity removable storage 300 can be used in conjunction with remote controller 200 as desired. Removable storage 300 may contain a write-protection notch or switch on its body to inform the removable storage interface 319 whether the removable storage 300 may be only read or whether it can additionally be written to, although such protective measures are not strictly necessary.

Figure 3A:
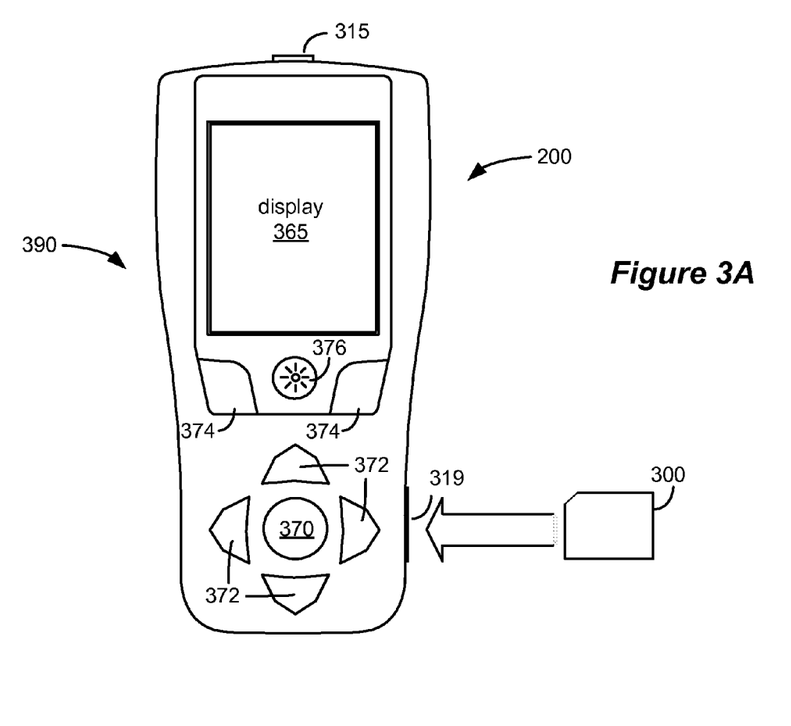
FIGS. 3A-3C are top, bottom, and side views of a remote controller for an implantable medical device according to one embodiment for storing contraindication information.
Figure 3B:
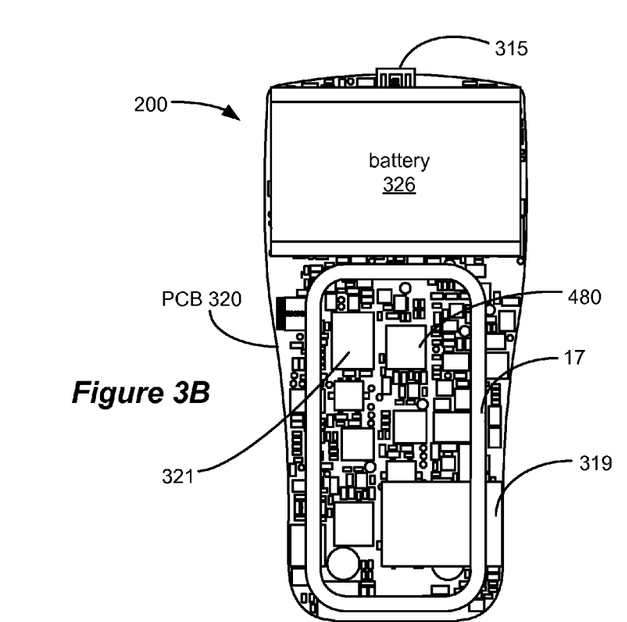
Figure 3C:
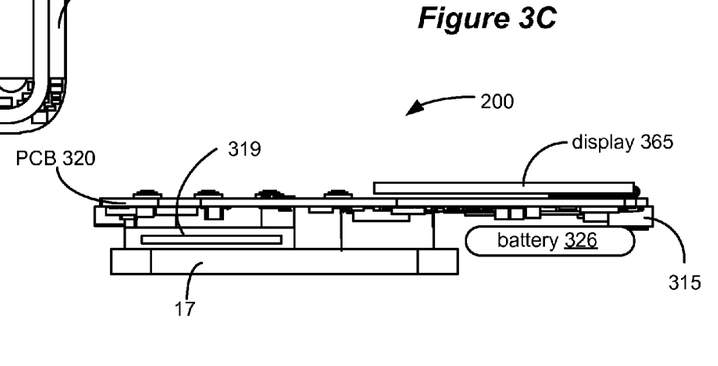

Turning to FIGS. 3B and 3C, bottom and side views of the remote controller 200 with its housing removed illustrate the removable storage interface 319 in relation to other elements of the remote controller 200. The removable storage interface 319 is preferably a read/write unit, allowing the remote controller 200 to read data previously stored on a removable storage 300, as well as write data to the removable storage 300. The position and orientation of the removable storage interface 319 are illustrative and by way of example only, and it can be positioned and oriented in any location or orientation that is convenient or desired. A slot in the housing of the remote controller 200 corresponding to a slot in the removable storage interface 319 allows insertion or extraction of the removable storage 300 into or out of the removable storage interface 319. In some embodiments, the removable storage interface 319 includes a protective cover over the slot (not shown). Although only a single removable storage interface 319 is shown, multiple interfaces can be included if desired.

In addition to the removable storage interface 319, the remote controller 200 typically include a user interface 390 (FIG. 3A), which generally includes a display screen 365, which can be a liquid crystal display (LCD) screen or any other display technology. Various buttons 370-376 on the user interface 390 can be used by the patient to operate the functions available with the remote controller 200. The arrangement, number, and positioning of buttons 370-376 are illustrative and by way of example only, and other indicator lights, buttons, or user interaction elements, including a numeric keypad or alphanumeric keyboard, can be provided by the remote controller 200 as desired. The user interface 390 may also include a speaker (not shown). As will be discussed further within, contraindication information can be accessed by a patient or clinician via the remote controller's user interface 390.

As best shown in FIG. 3B, the remote controller 200 can also include a non-removable storage 321 for providing data storage, which non-removable storage 321 can also include the contraindication information discussed earlier. Non-removable storage 321 is preferably non-volatile such as a flash EEPROM memory, but may also comprise a volatile memory such as an SRAM or DRAM memory. Non-removable storage 321 can also comprise other non-solid-state forms of storage as well, such as a hard disk, for example. Non-removable storage 321 can be in addition to, or as an alternative to, the removable storage 300 described above. The remote controller 200 can include multiple kinds of non-removable storage 321, some of which can be read-only memory, and some of which can be read-write memory. Operating software for the remote controller 200 is typically stored on the non-removable storage 321, including controlling communications with the IPG 100, driving the display 365, and reading data from and writing data to the removable storage 300 when coupled with the removable storage interface 319.

The remote controller 200 can also include a port 315 for wired communication with an external device, which port 315, like removable storage interface 319, can also be used as a means for receiving or transmitting contraindication information to or from the remote controller 200. Port 315 can in one example comprise a Universal Serial Bus (USB) port, although other types of ports can be used as desired for wired connectivity, including other types of serial ports, parallel ports, Ethernet ports, etc. The operating software for the remote controller 200 controls the port 315, including reading and writing data between the removable storage 300 and the port 315.

In addition to using the USB port 315 for wired communication, the USB port 315 can interface with a portable external removable storage device such as a USB thumb drive 510, as will be discussed further with respect to FIG. 6.

Where a removable storage 300 is used in conjunction with remote controller 200, the removable storage 300 can be loaded with therapeutic and diagnostic information externally to the remote controller 200 and then inserted into the removable storage interface 319 for use by the remote controller 200. For example, the manufacturer of the medical implant system can store the implant system manual(s) or contraindications on the removable storage 300 for use by the patient or clinician, who can in turn review the manual on the remote controller's display 365, or on another external computer as will be discussed in further detail later. Additionally, using a removable storage 300 to store contraindication information makes it easier for the manufacturer of the system to provide updated information to the patient. For example, if the manufacturer updates the manuals, perhaps by providing new contraindications or compatibilities, their implant customers can simply be sent a new removable storage 300 card in the mail, without requiring the remote controller 12 to network with other devices. For example, such a new card might contain the following new contraindication information: "Although the manufacturer previously recommended that patients not swim with their implant, or pass through X-ray machines, subsequent testing has shown these previously prohibited activities to be safe." Although new removable storage cards can be convenient, networking can also be very advantageous and convenient way of providing contraindication information to and from the remote controller 200, and comprises other embodiments discussed below.

Contraindication information can also be written to the removable storage 300 by the remote controller 200. In this scenario, the information (e.g., the manuals) can be resident in the remote controller 200 (e.g., in memory 321), or can be input (e.g., by a clinician) into the remote controller 200 via its user interface 390, or can be otherwise be communicated to the remote controller 200 from an external device such as a computer (e.g., particular clinician instructions or patient history regarding therapeutic or diagnostic techniques compatible or contraindicated by the patient's implant). In any event, once the contraindication information is stored on the removable storage 300 in this fashion, the removable storage 300 may then be removed from the remote controller 200 and taken to another computer platform (for example, a clinician's computer) to review that information, as explained further in connection with FIG. 6.

The non-removable storage 321 is similar to the removable storage 300, except of course as concerns its portability to other platforms. Thus, contraindication information can be written to the non-removable storage 321 by the remote controller 200 at manufacture or later times as just discussed, or the information can be read from the non-removable storage 321 for display at the remote controller 200 or for transmission to another platform.

Any convenient file format can be used for storing the contraindication information in the remote controller 200, including plain text files, structured files such as eXtended Markup Language (XML) files, Portable Data Format (PDF) files, or any other file format. The remote controller 200 in some embodiments is capable of displaying some or all of the stored information on the display 365, but the information stored by the remote controller 200 is not limited to information that is directly displayable by the display 365. For example, a PDF file of clinician information can be stored on the remote controller 200 even in embodiments that do not include software to display PDF files on the display 365. In such embodiments, the non-displayable information can be communicated to, accessed, and displayed by an external device such as the computer 500 illustrated in FIG. 6.

Additionally, the contraindication information stored with the remote controller 200 can include hypertext links to additional information, which can be accessed from the Internet (520; FIG. 6) by a web browser executed by an external computer used by the clinician. In some embodiments, the remote controller 200 can include web browser and network connectivity software allowing such links to be accessed while displaying the resulting information on the display 365.

Further shown in FIG. 3B is a wireless transceiver 480 that, like ports 315 and 319, can be used to receive or transmit contraindication information to or from the remote controller 200. Wireless transceiver 480 preferably enables a radio frequency (RF) link, such as a BLUETOOTH® or WI-FI® compliant link, but can also enable an optical link, such as an infrared link conforming to the specifications defined by the Infrared Data Association (IrDA). Additionally, communication coil 17, traditionally used as the antenna for communications with the IPG 100, can also be used as a communication link for carrying contraindication information to or from the remote controller 200, as discussed further in FIG. 6.

Figure 4:
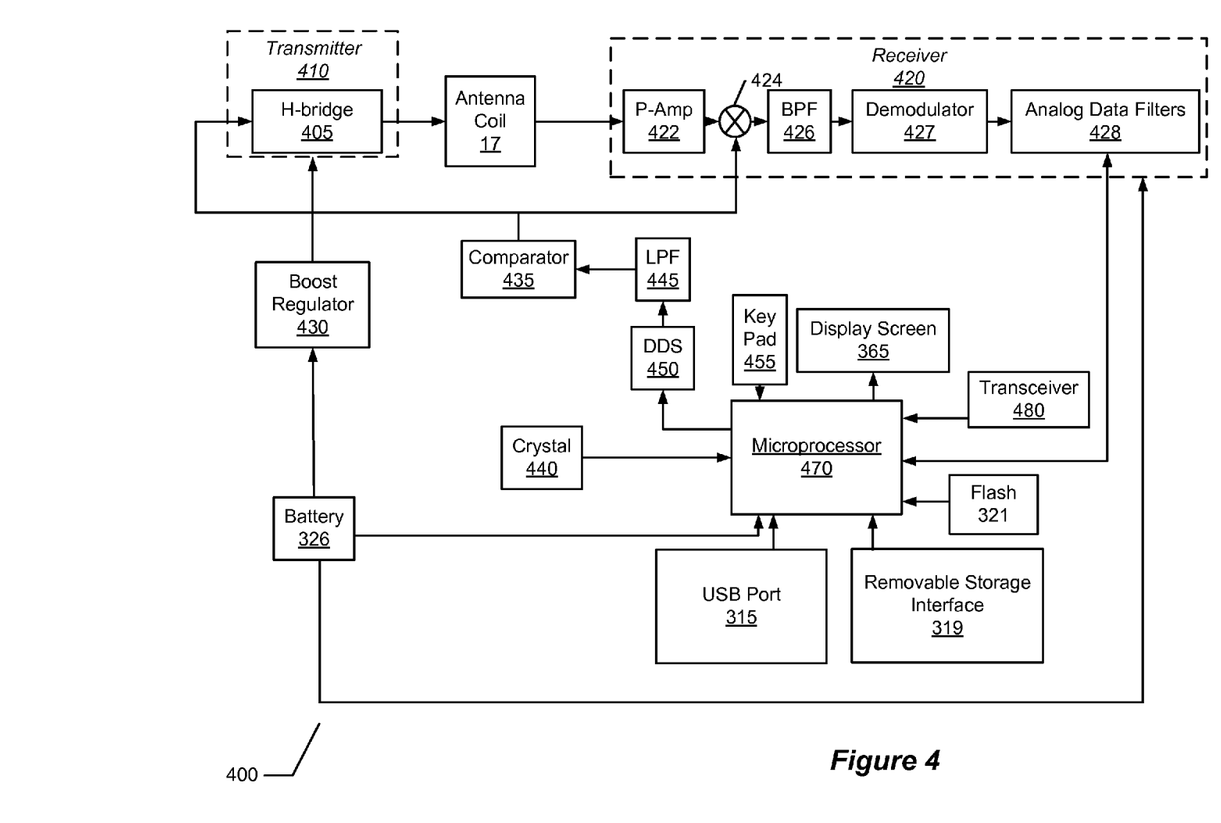
FIG. 4 is a block diagram illustrating an embodiment of circuitry elements for the remote controller of FIGS. 3A-3C.

FIG. 4 is a block diagram illustrating an embodiment of circuitry 400 for storing and communicating therapeutic and diagnostic information in the remote controller 200. A microprocessor 470 provides processing logic for the various features and functions of the remote controller 200, and as particularly relevant here, provides processing logic for reading, writing, and controlling the communication of the contraindication information, as well as for controlling the IPG 100, typically under the control of the operating software stored on the non-removable storage 321. Power to the remote controller 200 is provided by the battery 326.

The antenna coil 17 allows for communication with the IPG 100, such as for communicating therapy settings wirelessly to the IPG 100, or with other external systems as will be explained further below. The coil 17 can both transmit and receive information via transmitter 410 and receiver 420 respectively. Because the transmitter 410, receiver 420, and other associated illustrated components are well known in the art, they are not further discussed.

A crystal 440 provides clocking for the microprocessor 470. The display screen 365 provides the ability to display information to a user of the remote controller 200, including the contraindication information discussed herein. User interaction typically occurs through a key pad 455, which provides an interface to the buttons 370-376 discussed earlier. Also illustrated are USB port 315 and wireless transceiver 480 discussed previously, which are controlled by the operating software of the remote controller 200. Removable storage interface 319 and non-removable storage 321 discussed earlier are also illustrated as associated with the microprocessor 470.

Figure 5:
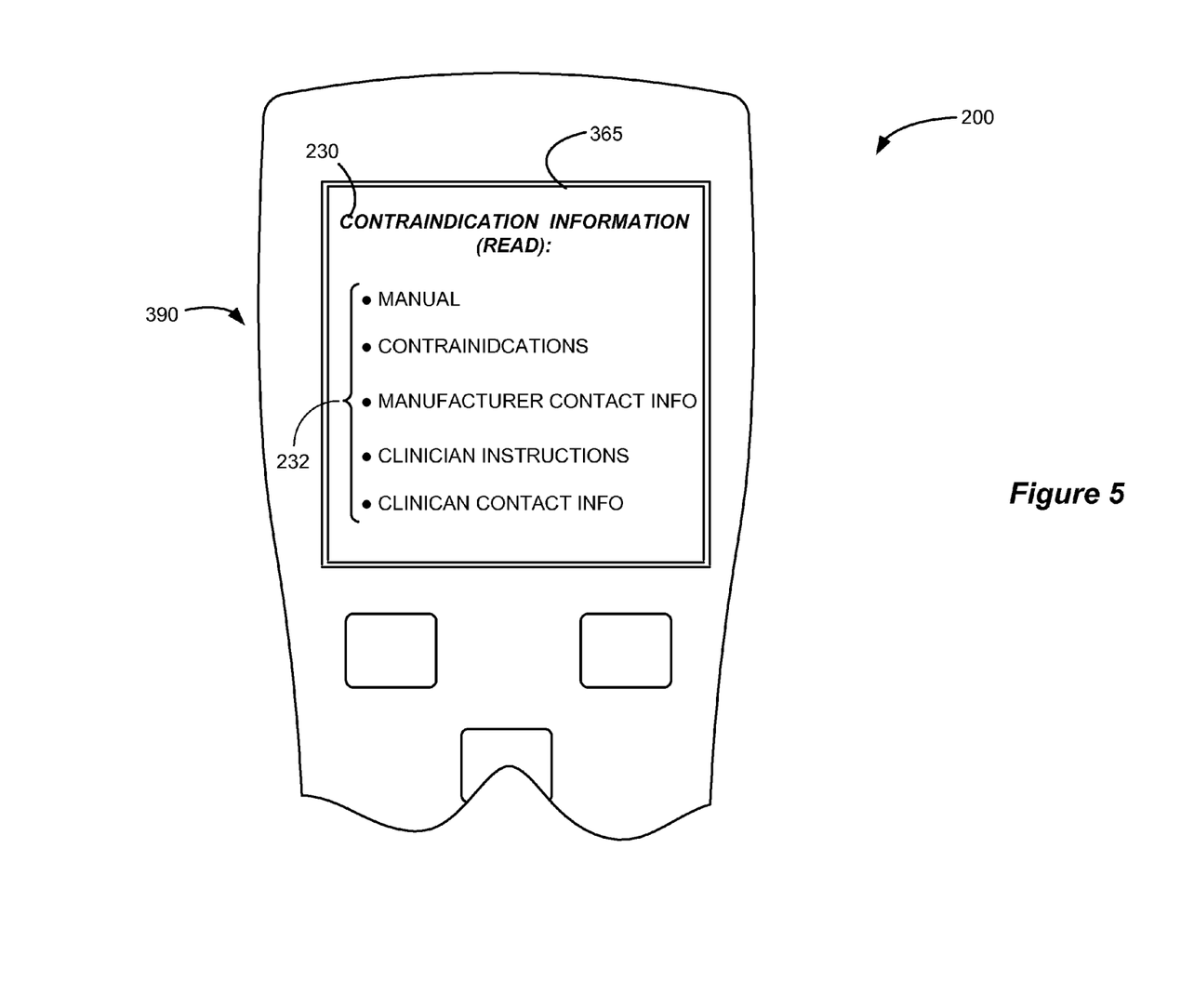
FIG. 5 is a user interface of the remote controller showing different ways of accessing the contraindication information.

FIG. 5 shows the user interface 390 on the remote controller 200 used to access the contraindication information. As shown, the contraindication information appears in a menu 230 on the remote controller's display 365, under which are listed several selectable types 232 of contraindication information mentioned previously, such as the manuals, contraindications, manufacturer contact information, etc. Menu 230 is designated as a "read" menu, meaning that the listed information types can only be read from this menu. However, a corresponding "write" menu (not shown) could allow these same information types to be written. The clinician or patient can select to review any of these types of information using the user interface's buttons as discussed earlier. For example, selection of "Contraindications" might reveal the following: "Because implant is near the patient's pelvis, MRI can only be used on the head and below the knees. No MRI should be taken of the patient's midsection. TENS should not be performed without first turning off the patient's implant using the remote controller." Selection of "Manual" may reveal this same information, although perhaps not as succinctly. Contraindication information stored with the remote controller 200 can also be conveyed to the patient or clinician using other aspects of the user interface 390, such by broadcasting the information in spoken form from a speaker for example.

The user interface 390 of the remote controller 200 may also be used to enter contraindication information. This might involve accessing the corresponding "write" menu discussed above, or otherwise manipulating the user interface 390 to allow the entry of contraindication information. For example, a clinician upon selecting (in the "write" menu) the option "Clinician Instruction" might input the following for the benefit of future clinicians: "The patient's implant is located in the upper right buttocks and contains a lead tunneled into the spinal cord. Please take precautions when performing surgery in this area. For more information, contact Dr. Lewis at [phone number]." Entering such information may require a user interface 390 having alphanumeric input capability, which means are well known. Once input, this new contraindication information is appropriately stored, e.g., in the removable storage 300 or non-removable storage 321, and then would be accessible via the corresponding entry in the "read" menu. Of course, having separate "read" and "write" menus for contraindication information is not required, and any other means of file management for reading and writing the information using the user interface can be used.

Figure 6:
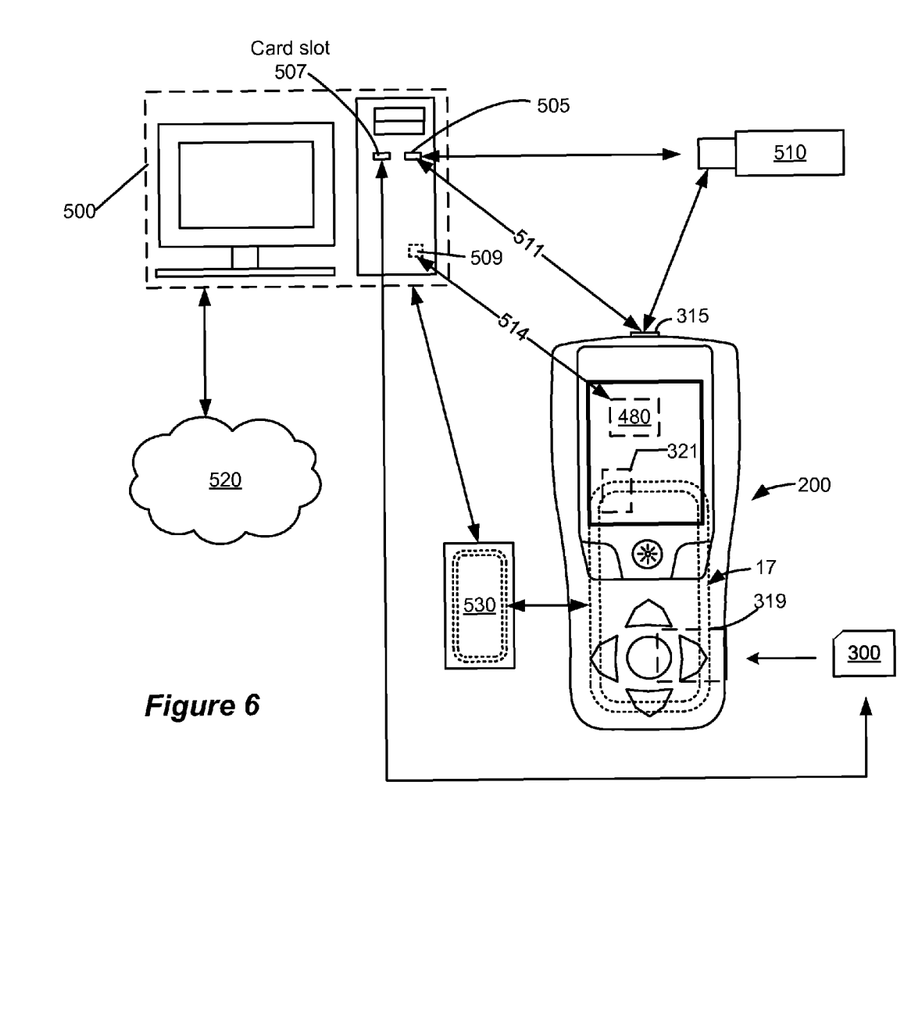
FIG. 6 is a block diagram illustrating a variety of communication paths for connecting the remote controller of FIGS. 3A-3C to an external device.

FIG. 6 shows various communication paths by which the contraindication information in the remote controller 200 can be remotely accessed by the patient or clinician. Such communication paths are especially useful when another external device is used to access the contraindication information, e.g., if the remote controller's user interface 390 (FIG. 3A) is not used for accessing the stored contraindication information at a given moment. Such communication paths are also useful when contraindication information is being written to the remote controller 200, for example, during manufacturing, upon implantation, or afterwards.

As shown, the remote controller 200 communicates with a computer 500. Computer 500 can comprise any generic computing device, and can differ depending on its context. For example, computer 500 can comprise a manufacturer's computer that is used during manufacture to write contraindication information (e.g., manufacturer contact information; manuals) into the memory (e.g., 321 or 300) associated with the remote controller 200. Computer 500 may also comprise a clinician's computer that is used to review contraindication information (again, e.g., manufacturer contact information; manuals) stored in the remote controller 200 (e.g., memories 300 or 321), or that is used to write new, additional, or updated contraindication information (e.g., e.g., clinician contact information; patient history) into the remote controller 200. Computer 500 can also comprise the patient's home computer.

Computer 500 can comprise any device capable of performing the disclosed communication techniques, including general purpose computers, special purpose clinical or manufacturing devices, portable computing devices such as PDAs or notebook computers, etc. Regardless, computer 500 can have connectivity to any suitable network 520, such as the Internet, which provides additional communication flexibility to the implant system as one skilled in the art will understand. For example, should the implant system manufacturer update the implant system manual(s) after its initial release, perhaps with new information regarding contraindications, this updated information may be downloaded from the Internet 520 to the remote controller 200 (e.g., memories 300 or 321) via computer 500 at future times.

As shown in FIG. 6, if the contraindication information is stored on a removable storage 300 associated with the remote controller 200, the clinician or patient can remove the removable storage 300 and insert it into a removable storage interface 507 on computer 500, which interface 507 can be similar to the removable storage interface 319 on the remote controller 200 discussed earlier. If the contraindication information is stored either in removable storage 300 or in non-removable storage 321, then that information could alternatively be sent to the computer 500 via a cable 511 coupled between port 315 on the remote controller 200 and port 505 on the computer 500. Such ports 315 and 505 can comprise USB ports, but as noted earlier, this is not strictly necessary. Once received at the computer 500, the contraindication information can be easily reviewed using the computer's user interface.

Contraindication information could also be wirelessly sent from either of memories 300 or 321 to the computer 500 via wireless link 514 using wireless transceivers 480 and 509 in the remote controller 200 and the computer 500 respectively. Contraindication information stored in memories 300 or 321 can also be transferred to computer 500 using a USB thumb drive 510. As is well known, and similar to removable storage 300, USB thumb drive 510 typically comprises non-volatile solid-state memory, although USB thumb drive 510 can also comprise a hard drive-based portable memory. Regardless, contraindication information can be transferred from the remote controller 200 to USB thumb drive 510 via port 315, after which the USB thumb drive 510 can be placed in port 505 on the computer 500 for review by the manufacturer, patient, or clinician.

In another embodiment shown in FIG. 6, contraindication information stored in memories 300 or 321 can be conveyed to the computer 500 using an intermediary coil 530 as shown in FIG. 6. Intermediary coil 530 can comprise a coil, which like coil 13 in the IPG 100 (see FIG. 2), can communicate with coil 17 in the remote controller 200 using magnetic coupling and a suitable modulation scheme such as FSK for example. Intermediary coil 530 can be hard-wired to computer 500, or can be linked to computer 500 through wireless means. Regardless, intermediary coil 530 allows contraindication information to be uploaded from the remote controller 200 to the computer 500, or vice versa, via magnetic induction by conveniently using the same communication coil 17 used to communicate with the IPG 100. If an intermediary coil 530 is used, other more specialized communication links (USB port 315; wireless transceiver 480) may not be necessary.

Once the contraindication information has been transferred to the computer 500, it can be conveyed to the user using the computer's user interface, e.g., the computer's display or speakers. Such computer interface can essentially mimic the functionality of the user interface 390 of the remote controller 200 illustrated earlier in FIG. 5, and thus is not redundantly illustrated. However, the added processing complexity of the computer 500 might allow for even more sophisticated manners of contraindication information review.

As mentioned earlier, an external device such as computer 500 can also be used to write contraindication information into the remote controller 200, i.e., to memory 300 or 321. This is advantageous for example when the manufacturer wants to program the manuals or contact information into the remote controller 200. If computer 500 comprises a clinician's computer, the clinician can use computer 500 to write patient-specific or non-patient-specific implant compatibilities or contraindications into the remote controller 200, which written information can then be reviewed by subsequent clinicians treating the implant patient (e.g., using menu 230; FIG. 6). For example, suppose the implant patient had a negative reaction to an MRI, such as uncomfortable heating of the implant. The clinician could use her computer 500 to download the following note to either of memories 300 or 321 in the remote controller 200: "Patient experienced discomfort relating to heating during MRI procedure of the pelvis. Use caution when MRI-ing this area. Recommend using powers lower than X when performing an MRI, especially on pelvis area."

Such writing of contraindication information from the computer 500 into the remote controller 200 (e.g., memories 300 or 321) can occur through the same bi-directional communication links discussed previously. For example, contraindication information can be written from the computer 500 to the remote controller 200 via card slot 507 to the removable storage 300; via USB port 505 using a wired connection 511 or a USB thumb drive 510; via wireless transceiver 509; via intermediate coil 530, etc. Once programmed into the remote controller 200, the contraindication information can be conveyed to the patient or clinician using the user interface 390 of the remote controller 200, or can subsequently be conveyed to the patient, clinician or other interested party via the computer 500.

Because the contraindication information stored in the remote controller 200 may comprise Protected Health Information (PHI), as that term is defined by the Health Insurance Portability and Accountability Act of 2003 (HIPAA), the remote controller 200 may be required to use encryption to protect the PHI. Various encryption techniques can be used, depending on the embodiment and the encryption techniques used by any external devices or systems with which the remote controller 200 communicates. Where the PHI is stored on a removable storage 300, then the PHI is typically encrypted as stored on the removable storage 300.

Because some contraindication information may not be suitable for patients, some embodiments of the remote controller 200 software can provide for password or other access controls over such information stored by the remote controller 200. The access controls can be embedded into the stored information itself or separately maintained in the file system on the storage device, whether removable or non-removable. In some embodiments, the remote controller 200 software can provide for accessing access-controlled information on the remote controller 200, such as by entering a password using one or more of the keys 370-374 or other such user interaction elements. In other embodiments, the access-controlled information cannot be opened on the remote controller 200, but can be accessed by an external device such as computer 500, using software on the external device to open the access-controlled information.

Embodiments of the improved remote controller 200 and the system in which it communicates were conceived in the context of providing easier access to contraindication information regarding implant patients needing to undergo a particular contraindication process. However, it should be noted that an improved remote controller 200 and system are not so limited, and that many different types of information could be stored at or communicated to or from the remote controller. Disclosed embodiments of the external device and its system should therefore not be limited to contraindication information unless so limited by the attached claims.

Moreover, the invention can be embodied in other external devices associated with a patient's implant. For example, a hand-held or portable external charger used to wirelessly recharge the battery in a patient's IPG 100 can also contain the contraindication information, and can function or be made to function as disclosed herein. An example of an external charger is disclosed in U.S. Patent Application Publication 2008/0027500 (pending).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for using an external device to communicate with an implantable medical device, comprising:
   using a user interface of the external device to wirelessly communicate with the implantable medical device by producing an electromagnetic field; and
   using the user interface to convey contraindication information for the implantable medical device reviewable by a user, wherein the contraindication information is stored in a storage of the external device.

2. The method of claim 1, wherein the user interface wirelessly communicates one or more of: therapy settings for the implantable medical device; a therapy program for the implantable medical device; data to increase or decrease stimulation strength of the implantable medical device; and data to shut off and turn on stimulation.

3. The method of claim 1, wherein the external device is hand-holdable and portable.

4. The method of claim 1, wherein the external device further comprises a removable storage interface or a port, and wherein the storage comprises a removable storage coupleable to the removable storage interface or the port.

5. The method of claim 1, wherein the storage is non-removable from the external device.

6. The method of claim 1, wherein the user interface comprises a display, and wherein the user interface conveys the contraindication information to the display.

7. The method of claim 1, further comprising receiving at the external device new, additional, or updated contraindication information, and storing the new, additional, or updated contraindication information in the storage.

8. The method of claim 1, wherein the contraindication information comprises information relevant to determining compatibility of at least one activity or procedure with the implantable medical device.

9. The method of claim 8, wherein the at least one activity or procedure comprises a medical therapeutic or diagnostic technique.

10. The method of claim 8, wherein the activity comprises a physical activity performable by a patient of the implantable medical device.

11. The method of claim 1, wherein the contraindication information comprises patient or clinician's manuals for the external device or the implantable medical device.

12. The method of claim 1, wherein the contraindication information comprises at least one activity or procedure contraindicated by the implantable medical device.

13. The method of claim 1, wherein the contraindication information comprises at least one activity or procedure compatible with the implantable medical device.

14. The method of claim 1, wherein the contraindication information comprises implantable medical device manufacturer or service representative contact information.

15. The method of claim 1, wherein the contraindication information comprises clinician contact information.

16. The method of claim 1, wherein the contraindication information comprises clinician instructions relevant to compatibility of at least one activity or procedure with the implantable medical device, or clinician instructions relevant to at least one activity or procedure contraindicated by the implantable medical device.

17. The method of claim 1, wherein the contraindication information comprises information specific to a patient of the implantable medical device.

18. The method of claim 1, wherein the external device comprises a coil, and wherein the external device wirelessly communicates with the implantable medical device using the coil to produce the electromagnetic field.

19. A method for communication in an implantable medical device system, comprising:
   using a first user interface of a first external device to wirelessly communicate with an implantable medical device by producing an electromagnetic field, wherein the first external device comprises a storage storing contraindication information for the implantable medical device; and
   conveying the contraindication information from the storage to a second external device, wherein the contraindication information is reviewable at a second user interface of the second external device.

20. The method of claim 19, wherein the first user interface wirelessly communicates one or more of: therapy settings for the implantable medical device; a therapy program for the implantable medical device; data to increase or decrease stimulation strength of the implantable medical device; and data to shut off and turn on stimulation.

21. The method of claim 19, wherein the first external device is hand-holdable and portable.

22. The method of claim 19, wherein the first external device further comprises a removable storage interface or a port, and wherein the storage comprises a removable storage coupleable to the removable storage interface or the port.

23. The method of claim 22, wherein the contraindication information is conveyed from the storage to the second external device by removing the removable storage from the removable storage interface or the port and coupling the removable storage to a removable storage interface or a port of the second external device.

24. The method of claim 19, wherein the first and second external devices each comprises a port, and wherein the contraindication information is conveyed from the storage to the second external device by a cable coupled to the ports of the first and second external devices.

25. The method of claim 1, wherein the first external device further comprises a first antenna, wherein the contraindication information is wirelessly conveyed from the storage to the second external device by the first antenna.

26. The method of claim 25, wherein the first external device wirelessly communicates with the implantable medical device using the first antenna to produce the electromagnetic field.

27. The method of claim 25, wherein the first external device comprises a second antenna, wherein the first external device wirelessly communicates with the implantable medical device using the second antenna to produce the electromagnetic field.

28. The method of claim 19, wherein the storage is non-removable from the first external device.

29. The method of claim 19, wherein the second user interface comprises a display, and wherein the contraindication information is reviewable at the display.

30. The method of claim 19, wherein the second external device is connected to a network, wherein the contraindication information is conveyed from the storage to the network, and wherein the contraindication information is further conveyed from the network to the second external device.

31. The method of claim 30, wherein the network comprises the Internet.

32. The method of claim 19, wherein the contraindication information is conveyed from the storage to the second external device using a protocol used by the first external device to wireless communicate with the implantable medical device by producing the electromagnetic field.

33. The method of claim 19, wherein the contraindication information comprises information relevant to determining compatibility of at least one activity or procedure with the implantable medical device.

34. The method of claim 33, wherein the at least one activity or procedure comprises a medical therapeutic or diagnostic technique.

35. The method of claim 33, wherein the activity comprises a physical activity performable by a patient of the implantable medical device.

36. The method of claim 19, wherein the contraindication information comprises patient or clinician's manuals for the first external device or the implantable medical device.

37. The method of claim 19, wherein the contraindication information comprises at least one activity or procedure contraindicated by the implantable medical device.

38. The method of claim 19, wherein the contraindication information comprises at least one activity or procedure compatible with the implantable medical device.

39. The method of claim 19, wherein the contraindication information comprises implantable medical device manufacturer or service representative contact information.

40. The method of claim 19, wherein the contraindication information comprises clinician contact information.

41. The method of claim 19, wherein the contraindication information comprises clinician instructions relevant to compatibility of at least one activity or procedure with the implantable medical device, or clinician instructions relevant to at least one activity or procedure contraindicated by the implantable medical device.

42. The method of claim 19, wherein the contraindication information comprises information specific to a patient of the implantable medical device.

* * * * *